United States Patent
Zakharov et al.

(10) Patent No.: US 12,228,802 B2
(45) Date of Patent: Feb. 18, 2025

(54) APPARATUS AND A METHOD FOR CUSTOMISING AN OPTICAL LENS

(71) Applicant: VIVIOR AG, Zurich (CH)

(72) Inventors: Pavel Zakharov, Volketswil (CH); Michael Mrochen, Zug (CH)

(73) Assignee: Carl Zeiss Vision GmbH, Aalen (DE)

(*) Notice: Subject to any disclaimer, the term of this patent is extended or adjusted under 35 U.S.C. 154(b) by 849 days.

(21) Appl. No.: 17/053,894

(22) PCT Filed: Apr. 23, 2019

(86) PCT No.: PCT/EP2019/060274
§ 371 (c)(1),
(2) Date: Nov. 9, 2020

(87) PCT Pub. No.: WO2019/219334
PCT Pub. Date: Nov. 21, 2019

(65) Prior Publication Data
US 2021/0247626 A1    Aug. 12, 2021

(30) Foreign Application Priority Data
May 16, 2018    (EP) .................................... 18172663

(51) Int. Cl.
*G02C 7/02*    (2006.01)
*A61B 3/00*    (2006.01)
(Continued)

(52) U.S. Cl.
CPC ............ *G02C 7/027* (2013.01); *A61B 3/0025* (2013.01); *A61F 2/16* (2013.01); *G02C 7/025* (2013.01); *G02C 7/04* (2013.01)

(58) Field of Classification Search
CPC .......... G02C 7/027; G02C 7/025; G02C 7/04; A61B 3/0025; A61F 2/16
(Continued)

(56) References Cited

U.S. PATENT DOCUMENTS

2015/0286070 A1* 10/2015 Aikawa ............... G02B 27/0093
351/159.76

FOREIGN PATENT DOCUMENTS

WO    WO-2009076670 A1 *  6/2009  .......... A61F 2/1618
WO    2010028654 A1    3/2010
(Continued)

OTHER PUBLICATIONS

European Patent Office, International Search Report and Written Opinion for PCT/EP2019/060274, dated Jul. 8, 2019.
(Continued)

*Primary Examiner* — James R Greece
(74) *Attorney, Agent, or Firm* — Williams Mullen; Thomas F. Bergert

(57) ABSTRACT

The present disclosure relates to an apparatus (100) for customising an optical lens which comprises an observation unit (130) adapted to acquire at least one of visual activities of a user and viewing distance profiles of the visual activities, a processor (170) adapted to calculate a personal distance profile based on at least one of the acquired visual activities and the acquired viewing distance profiles, and an implementation unit (190) adapted to customise the optical lens based on at least one of the acquired visual activities and the acquired personal distance profile.

12 Claims, 9 Drawing Sheets

(51) Int. Cl.
*A61F 2/16* (2006.01)
*G02C 7/04* (2006.01)

(58) Field of Classification Search
USPC ..................................................... 351/159.74
See application file for complete search history.

(56) References Cited

FOREIGN PATENT DOCUMENTS

| WO | 2016087914 A1 | 6/2016 | |
|---|---|---|---|
| WO | WO-2017042824 A1 * | 3/2017 | ........... A61B 3/0025 |
| WO | 2017174508 A1 | 10/2017 | |

OTHER PUBLICATIONS

Chinese National Intellectual Property Administration, Chinese Examination Report for Application No. 2019800322720, Nov. 13, 2024.

* cited by examiner

APPARATUS AND A METHOD FOR CUSTOMISING AN OPTICAL LENS

CROSS-REFERENCE TO RELATED APPLICATIONS

This application is the U.S. national phase of international application PCT/EP2019/060274, filed on Apr. 23, 2019, which claims the benefit of European application EP 18172663.9 filed on May 16, 2018; all of which are hereby incorporated herein in their entirety by reference.

TECHNICAL FIELD

The present disclosure generally relates to the field of designing optical lenses. More particularly, the present disclosure relates to an apparatus and a method for customising an optical lens according to behaviours or requirements of a patient or user.

BACKGROUND

As one of the currently available solutions for eyesight correction, intraocular lenses (IOL) can be implanted into patients' eyes to replace natural crystalline lenses when they are clouded (e.g. condition called cataract), when their performance is not sufficient (e.g. presbyopia, called refractive lens exchange) or when they are damaged.

Currently, IOLs are premade and are coming in 0.5 Diopter steps. Some patients, however, might have additional optical insufficiencies, like aberrations and astigmatism, which cannot be corrected by way of such standard IOLs. IOLs delivering sharp images at one specific distance/optical power are called monofocal. Further, there exist IOLs with advanced optics which allow to focus light from multiple or from a range of distances, such as bi-focal, trifocal and multifocal IOLs.

In order to address the patients' potential needs, a clinic or the like is required to have hundreds or even thousands of various types of lenses in store. To achieve even finer resolution would require much larger inventory. However, this seems difficult if not impossible for clinics let alone small clinics.

Moreover, from the patients' perspective, there are needs to have more precise lenses both in terms of resolution and in terms of customisation of optical properties of individual patients.

In recent years, progress has been made in fine tuning lenses in order to better match the target refraction as well as in producing lenses on the spot with modern manufacturing techniques. Fine tuning of lenses can be performed before implanting them as well as after implantation.

The same applies to a modification of natural lenses of the eye with refractive surgery, e.g. performed by laser on the corneal surface. The laser settings and treatment geometry can be customised with high accuracy to achieve the required visual outcome.

However, current practice of estimating the refractive targets in a clinic by interviewing patient is insufficient to reflect the needs of the individual patients. Even with ultimate customisation no lens can provide perfect vision correction under all conditions. For example, modern lenses can deliver high image quality at one or more viewing distances, while on the other distances patient has to tolerate reduced visual acuity or use additional vision corrective means, like spectacles. Thus, there exists the need for patients and/or surgeons to fully and correctly understand the needs of the individual patients to define the refractive target and thus properly adjust the respective lenses in order to maximise benefits of such solutions.

It is thus an object of the present disclosure to provide more precise and efficient ways to customise an optical lens, e.g. an IOL or laser-treated cornea, which is ideally more suitable for the individual patients as well.

SUMMARY

According to an aspect of the present disclosure, an apparatus (e.g. a lens customizing/customization device or a lens design device) for customising an optical lens is provided. The apparatus comprises an observation unit, a processor and/or an implementation unit. The observation unit is adapted to acquire visual activities of a user and/or viewing distance profiles of the visual activities. The processor is adapted to determine or calculate a personal distance profile based on the acquired visual activities of the user and/or the acquired viewing distance profiles. The implementation unit is adapted to customise the optical lens based on the visual activities of the user and/or the acquired personal distance profile.

The personal distance profile may be defined to include or be at least one of a statistical distance profile and a preferred distance profile.

The optical lens is generally understood in the present disclosure as an optical device which is meant to improve user's vision. Lens may be any of the natural eye structures, such as corneal or crystalline lens surfaces, lens may be external to the eye, such as spectacles or contact lens, or may also be implanted in the eye, such as an intraocular lens (IOL), or may be a combination of aforementioned lenses.

A visual activity may be defined as an activity performed by the user or patient. The visual activity may involve (rely on) vision, for example, reading, working on computer or watching TV. Performance of the visual activity crucially but not exclusively depends on performance of the patient's vision. The visual activity is not necessarily limited to the activity of a visual system, but might also involve other physiological systems, for example, shooting relies on sharp vision, but also involves the muscular system among others. Or the visual activity may be simply defined as an activity for which vision of the user is required.

A viewing distance profile may be defined as an occurrence distribution of viewing distances. It may show the frequency of the viewing distances employed by the patient or user. The viewing distance profile may be also understood as a distribution of any parameter derived from viewing distance, e.g. optical or refractive power of the lens defined as reciprocal of viewing distance. The viewing distance profile can be related to a specific visual activity of the individual or to a number of visual activities.

A viewing distance may be defined as a distance between the eyes or eye structures of the user or any other reference point related to the eyes and an object existing in the visual range or activity of the user.

An activity distance profile may be defined as a viewing distance profile specific for a visual activity. The activity distance profile may be acquired by an actual estimation of the viewing distance profile that occurs during the visual activity or retrieving a typical distance profile pre-defined based on typical behaviours of population during the visual activity.

A personal distance profile may be defined as a distribution of the visual performance (of the visual solution) as a function of the viewing distances. The personal distance profile may reflect the personal/individual lifestyle and personal preferences of the patient or user.

A statistical distance profile may be defined as accumulation of the activity distance profiles each of which is weighted by a time spent on a visual activity related to one of the viewing distance profiles.

A preferred distance profile may be defined as accumulation of the activity distance profiles each of which is weighted by an activity relevance factor that reflects preferences of the user.

The personal distance profile may be described as a 2-dimensional graph where the x-axis denotes optical powers or viewing distances, and the y-axis denotes the frequency of usage of corresponding distances or optical powers.

By way of the above customising process(es), an optical lens reflecting the user's needs regarding the visual activities of the user can be efficiently selected or customised.

For example, the observation unit may be further adapted to estimate a time spent on each of the visual activities. The processor may be further adapted to calculate the statistical distance profile based on the acquired viewing distance profiles and a ratio of the estimated time spent on each of the visual activities to a total time of the visual activities. The implementation unit may then be adapted to customise the optical lens based on the personal distance profile including the statistical distance profile.

In the patient's daily life plurality of visual activities are usually carried out. However, the time spent on each visual activity is individual and thus importance of the visual activity can be derived from the average relative time spent in a specific visual activity by the respective patient. The relative time can be estimated as the ratio of the time spent on the specific visual activity with respect to a total time of the multiple visual activities. The relative time can be considered for determining or calculating the statistical distance profile. Specifically, the ratio for the specific visual activity can be multiplied with an activity distance profile of the specific visual activity so that a weighted activity distance profile can be derived. Weighted activity distance profiles for the multiple visual activities can be integrated for calculating the statistical (time-based) distance profile.

The observation unit may be adapted to acquire activity relevance (AR) factors estimated from at least one of an input of the user, a frequency of spectacle usage and changes, an amount of motion of the user, an illumination in a location of the user and general preferences (of the users) for the spectacle independence. The processor may be adapted to calculate the preferred distance profile based on the acquired viewing distance profiles and the acquired activity relevance factors. The implementation unit may then be adapted to customise the optical lens based on the personal distance profile including the preferred distance profile.

In this way, the patient's needs can be more precisely reflected to or by the customisation of the optical lens. In other words, customised optical lens can more precisely reflect the patient's needs based on the preferred distance profile.

The activity relevance factor may be measured or input through the observation device or input unit of the apparatus.

The activity relevance factor may be defined as needs or preferences for the use of vision without spectacles or any other additional vision correcting means during the specific activity. For example, during sports activities, for the reason of comfort, or social activities, for cosmetic reasons, it may be important for the patient or user to be able to function without spectacles. This would result in the high AR for such activities. Alternatively, during prolonged periods of sedentary reading or working on personal computer patient might be more prepared to tolerate additional vision correcting device as spectacles, and thus the uncorrected vision relevance can be low.

The activity relevance factor may be estimated for the user objectively, subjectively or both. The activity relevance factor can be derived from a direct subjective patient input (individual preferences), can be regarded as the time spent during observations (direct translation from), can be based on standard generalized distributions and/or can be derived from observations based on objective spectacles discomfort criteria.

The subjective input by the patient (individual preferences) can be taken before and/or after measurements during the solution planning (as an input through a GUI of the processing computer program, for example) or in real time during the visual activities (through a user interface of the device or accompanying journaling means). Accompanying journaling means can be a mobile application or a traditional notebook. Individual preferences may reflect the requirements of the patient to be spectacles free (spectacles independence). Such requirements can be caused by comfort considerations, like reluctance to wear spectacles during favourite sports activities or during swimming, or by aesthetics considerations, e.g. when the patient intends to appear younger without spectacles.

For example, the activity relevance factor may be inferred by a frequency of spectacle changes while performing the visual activities. The spectacle changes can be estimated from the observations (by the observation unit) as the number/frequency of switching between vision zones. For example, driving employs far distance vision for objects outside the car and near/intermediate vision for dashboard as well as dials. Changing spectacles in this situation would be impractical, and a visual correcting solution would be better to target minimisation of the discomfort, hence the AR factor may be high for such visual activities.

Another example of the objective discomfort criteria can be an amount of vigorous motions during visual activities. The amount of the motions can be estimated from measurements of the inertia sensors, such an accelerometer, a gyroscope, a magnetometer, a step counter or etc. or from location tracking sensors which can be equipped in the apparatus. Presence of the vigorous activity may suggest the requirement of the spectacles independence and thus for high uncorrected visual acuity, since the patient might have difficulty wearing the spectacles in such visual activities. Hence, the AR factor for this visual activity may be set with a high value.

Yet another, criteria for the activity relevance factor can be the illumination conditions during the visual activities. Illumination conditions during the visual activities are responsible for a change of the patient's pupil size and thus it may be considered when selecting the lens geometry. For example, if a patient is performing visual activities in low light conditions (mesopic or scotopic) and when his/her pupils is/are significantly dilated, it may be recommendable that the solution for the eyesight correction involves a large optical zone in order to avoid distortions caused by light passing outside of the optical zone of the lens. On contrary, in a well-lighted condition (photopic vision), the pupil would be significantly constricted, which results in extended optical depth of the field and thus allows for higher tolerance to visual defocus. Thus the vision correcting strategy might be tuned to benefit activities/distances for the low-light conditions, while compromising on the activities/distances performed in the bright-light.

Visual activities performed in low-light are likely more vision demanding and would require better vision optics to provide a sharp vision, while visual activities in bright-light are more defocus-tolerant. The colour content of image-forming light may also influence the contrast sensitivity of an eye. Thus, AR factor would be higher for the low-light visual activities and lower for the bright-light visual activities. Hence, the AR factor for the low-light visual activities may be set to a higher value, and the AR factor for the bright-light visual activities may be set to a relatively lower value.

Extended periods of a vision activity with limited motion would result in low objective discomfort with spectacles, and thus lead to a low AR value. Such visual activity can be reading, working on the desktop computer, watching TV etc.

One can also use general (population-derived) activity relevance factors (i.e. general factors). For example, if the majority of the population chooses spectacle independence during tennis (sport activity), a high AR factor can be assigned to this visual activity. General preferences can be stored in a predefined static database, where data is updated from external sources (like manual input by supporting personal or automatically updated from external databases). Alternatively, general preferences can be stored in a dynamic database updated by the system (e.g. the lens customising device) itself based on the other inputs to the AR factor, like other patients' inputs or objective measurements of relevance. In a more general manner, observations of the patient behaviour can be collected as a set of sensor measurements, which further serve as inputs to the algorithm which automatically assigns an individual to one of the typical groups and thus derives a solution/strategy optimal for such a group.

In one embodiment, the statistical (time-weighted) distance profile $H_t(P)$ may be defined as:

$$H_t(P) = \frac{1}{T} \sum_{a \in A} t_a h_a(P),$$

wherein T is the total time of the visual activities, $t_a$ is the time spent on a visual activity of the visual activities, P is a viewing distance, an optical power or a defocus or any distance-related parameter, $h_a(P)$ is a viewing distance profile for the visual activity, a is the visual activity, and A stands for all visual activities.

The preferred (relevance-weighted) distance profile $H_m(P)$ may be defined as:

$$H_m(P) = \sum_{a \in A} m_a h_a(P),$$

wherein $m^a$ is an activity relevance factor for a visual activity, and is normalised as $$\sum_{a \in A} m_a = 1$$

when a is the visual activity and A is the set of visual activities, P is a viewing distance, an optical power or any distance-related parameter, and $h_a(P)$ is a viewing distance profile for the visual activity.

Further, $h_a(P)$ may be defined as a viewing distance profile for a visual activity (i.e. an activity distance profile) which may be observed (measured) by the apparatus or received as the typical distance profile.

The acquired viewing distance profiles may be either of actual activity distance profiles or typical activity distance profiles. Herein the actual activity distance profiles may be measured while the user performs the visual activities, and the typical activity distance profiles may be pre-defined distance profiles determined based on typical behaviors of a population during the visual activities.

The apparatus may further comprise an activity sensing unit that may be adapted to measure distances to a plurality of points of at least one object, determine orientations and/or positions of the activity sensing unit, derive information about the at least one object based on the measured distances and the determined orientations and/or positions, and classify the visual activities of the user based on the derived information. The information about the at least one object comprises or is at least one of a position, a shape, an inclination and a size of the object.

For example, the optical lens may be customised by the implementation unit which may be adapted to determine the optical parameters of the lens from the statistical (time-weighted) distance profile and/or the preferred (relevance-weighted) distance profile, and select or manufacture the optical lens having the required optical parameters.

For example, if the distance profile has a pronounce maximum at the certain distance the best IOL implementation would be the monofocal lens which after being implanted into patient eye delivers best visual acuity at the identified distance.

According to another aspect of the present disclosure, a method for customising an optical lens is provided. The method may comprise acquiring visual activities of a user and/or acquiring viewing distance profiles of the visual activities, acquiring a personal distance profile based on the acquired visual activities of the user and/or the acquired viewing distance profiles, and customising the optical lens based on the acquired visual activities of the user and/or the acquired personal distance profile. The personal distance profile may include or be at least one of a statistical distance profile and a preferred distance profile.

The method may further comprise estimating a time spent on each of the visual activities, and calculating the statistical distance profile based on the acquired viewing distance profiles and a ratio of the estimated time to a total time of the visual activities.

The method may further comprise acquiring activity relevance factors based on parameters including at least one of an input of the user, a frequency of spectacle usage and changes, an amount of motion of the user, an illumination in a location of the user and general preferences for the spectacle independence, and calculating the preferred distance profile based on the acquired activity relevance factors.

The statistical distance profile and the preferred distance profile may be respectively defined in the same way as described above.

Further, the acquired viewing distance profiles may be either actual activity distance profiles or typical activity distance profiles. The actual activity distance profiles may be measured while the user performs the visual activities. The typical activity distance profiles may be pre-defined distance profiles determined based on typical behaviours of population during the visual activities.

Customising the optical lens may comprise determining the number of focal points needed in at least one of the statistical distance profile and the preferred distance profile, determining optical power for the focal points, determining light distribution between focal points, and selection or manufacturing the optical lens having the determined optical power at the focal points.

For example, selection of the lens geometry can be performed by matching the profiles (defocus curves) of available and/or implementable lens geometries to the required distance profile. Such matching can be done by the means of least square fitting of the desired and implementable profiles or by any other statistical technique.

In the simple case of distance profile with a single pronounced peak, the monofocal lens matching produces the single best focal point with the optical power corresponding to the peak of preferred viewing distance.

The outcome of lens geometry matching can be a lens template and parameters of adjustment/fine-tuning of such lens. Such parameters may be in the form of setting of technological parameters for implementation of required geometry, such as laser power, laser wavelength, timing and geometry setting. For the case of IOL manufacturing such parameters may include the ablation profile of selected PMMA template. For case of refractive surgery such parameters may include the geometry of corneal ablation profile. For the case of adjustable IOL such parameters may include the intensity, geometrical distribution and exposure of light, magnetic field or other influence responsible for optical power adjustment. For the case of corneal cross-linking such parameters may include an intensity, geometrical distribution of ultraviolet illumination as well as time of exposure. It is also possible that the selected template requires minimal fine-tuning or no adjustment at all, in this case selection of the implementation strategy is reduced to selection of the template from the database of lens templates.

The adjustment/fine-tuning of the optical lens can be performed before and/or after surgery or implantation. Correspondingly adjustments of the tuning parameters can be performed based on the results of surgery or implantation, for example, when the position of the lens within eye structure has been stabilised after IOL implantation or corneal surface stabilised after refractive surgery.

It is understood that selection of parameters of customisation is also influenced by the parameters of technological process involved in the lens shaping, for example, ablation rate of the material used, type of the laser used for ablation, refractive index of the material, geometrical limitations, etc. Thus parameters of customisation process can also be included in the implementation selection process.

Selection of the lens design template and customisation are also influenced by the individual parameters of visual system of the patient. For example, the required optical power of the IOL is influenced by eye geometry, in particular, by eye length, corneal optical power, white-to-white corneal diameter, anterior chamber depth, natural lens thickness, etc. Any of those parameters or any combination can be included in the lens design process.

In another implementation, design of the spectacles lens can include the interpupillary distance, vertex distance, prescription, etc.

The method may be performed for a group of users. In this case, the method comprises acquiring visual activities and/or personal distance profiles for the group of users. The method further comprises customising the optical lens based on the statistical processing of personal distance profiles or based on statistical processing of the acquired visual activities and/or the acquired personal distance profiles for the group of users.

The statistical processing may be an averaging of the profiles of the users in the group performed with arithmetic mean:

$$H^N(P) = \frac{1}{N}\sum_i H^i(P),$$

where $H^i(P)$ is a personal (time-weighted or preferred) distance profile of a user i from a group of N users and $H^N(P)$ is a group-averaged distance profile. Processing may be a weighted averaging of the personal profiles, a robust averaging of the profiles performed with the median processing, or any other processing which allows obtaining distance profile best matching the requirements of the users in the selected group. Alternatively, processing can be configured to identify distance profiles of the users (outliers), which are not adequately addressed by the existing templates and further develop lens templates which would be optimised for the identified users.

The statistical processing may be configured to analyse viewing distance profiles for at least one selected activity from the group of users in order to develop lens design which would best match the requirements of the selected activities. The statistical processing can be performed with arithmetic mean:

$$h_a^N(P) = \frac{1}{N}\sum_i h_a^i(P),$$

where $h_a(P)$ is the distance profile of an activity a of a user i and $h_a^N(P)$ is a group-averaged distance profile of an activity a. Processing may be done with any other statistical technique which allows obtaining distance profile best matching the requirements of the users in the selected group for the selected activities.

The group-averaged distance profile may be further used to design the lens geometry which implements required viewing distance distribution in similar way as it is performed for personal distance profile by determining the number of focal points needed in group-averaged distance profile, determining optical power and light distribution for the focal points, and manufacturing the optical lens having the determined optical power at the focal points.

In another implementation, lens design may be performed based on the plurality of distance profiles of the group. The number, positions and the light distribution of the focal points may be determined from the complete set of distance profiles. For example, the first focal point of the lens may be identified as a first most frequently occurring distance peak in the personal distance profiles of a group. In a similar way, the second focal point may be identified as a second most frequently occurring distance peak in the personal distance profiles and so on.

Herein, the optical lens may be any of natural optical elements of an eye, an ophthalmic implant and an ophthalmic lens. Herein, the ophthalmic lens may be one of an intraocular lens, a contact lens and a spectacles lens, the ophthalmic implant may be one of an intraocular lens, corneal inlay, corneal onlay, corneal transplant, retinal implant and visual prosthesis. The natural optical element of an eye may be a cornea, a crystalline lens and retina. Modification of natural optical element and implementation of required lens design is performed with the eye surgery.

By way of the above mentioned features, the present apparatus and method according to the first and second aspects are able to provide more precise and efficient ways to customise the optical lens which is ideally be more suitable for individual patients or users.

Specific examples or explanations for the method may be complemented by the explanations described above for the passive scanning device in the present disclosure.

BRIEF DESCRIPTION OF THE DRAWINGS

In the following, the present disclosure will further be described with reference to exemplary implementations illustrated in the figures, in which.

DETAILED DESCRIPTION

In the following description, for purposes of explanation and not limitation, specific details are set forth in order to provide a thorough understanding of the present disclosure. It will be apparent to one skilled in the art that the present disclosure may be practiced in other implementations that depart from these specific details.

Those skilled in the art will further appreciate that functions explained herein below may be implemented using individual hardware circuitry, using software functioning in conjunction with one or more processors, e.g. a programmed microprocessor or a general purpose computer, using an Application Specific Integrated Circuit (ASIC) and/or using one or more Digital Signal Processors (DSPs). It will also be appreciated that when the present disclosure is described as a method, it may also be embodied in a computer processor arrangement and a memory arrangement coupled to a processor arrangement, wherein the memory arrangement is encoded with or stores one or more programs or corresponding code to cause the processor arrangement to perform or control the methods disclosed herein when executed by the processor arrangement.

Figure 1:
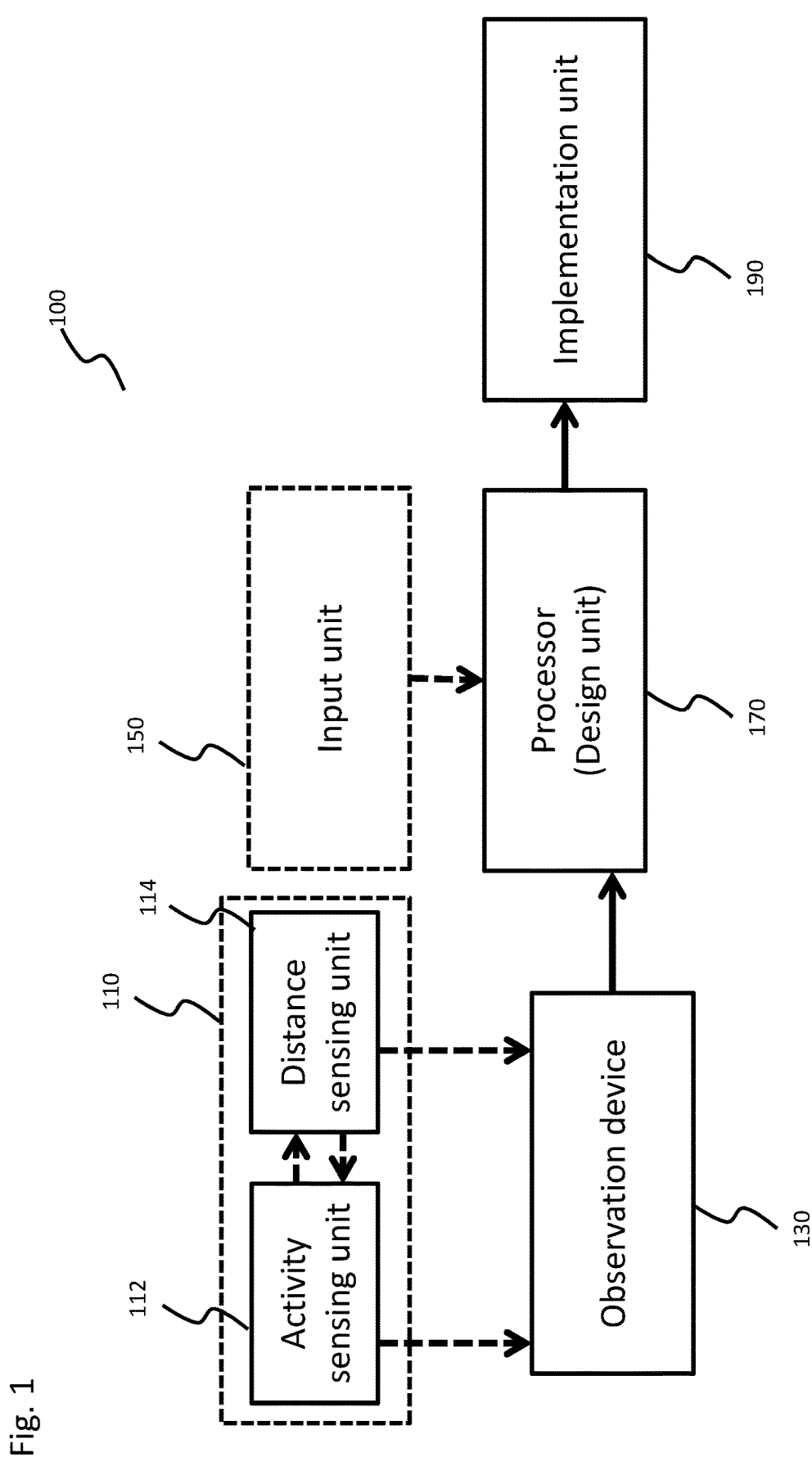
FIG. 1 illustrates an example of a lens customising device according to the present disclosure.

FIG. 1 illustrates an example of a lens customising device according to the present disclosure. In the present example, the lens customising device 100 may comprise an observation device 130, a processor 170, and/or an implementation unit 190. The lens customising device may further comprise a scanning device 110 and/or an input unit 150. The scanning device 110 may comprises an activity sensing unit 112 and/or a distance sensing unit 114.

The scanning device 110 may measure or derive visual activities and/or viewing distance profiles. For understanding and/or deriving the visual activities and time spent, various approaches can be used, such as wearable motion sensors (accelerometer, gyro, etc.) containing an algorithm capable of recognizing the visual activities. One approach can also be a wearable camera or camera observing the user. For obvious reasons, identification of the visual activities would benefit from sensors directly related to vision, such as sensors for the viewing distance, eye tracking, blinking, pupils size, accommodation effort, head tilt, as well as sensors of physiological state. One or more devices that may perform the above one or more functions can be included in the lens customising device or the scanning device. Or the above one or more functions can be performed in one or more devices included in the lens customising device or the scanning device described above. The scanning device 110 can be implemented in the observation unit 130.

The activity sensing unit 112 may measure or derive visual activities of the user (or patient) who is using the scanning device 110. The measured visual activities can be abstractive or concrete. The abstractive visual activities can be measured or derived by merely distinguishing visual activities having significant changes in the measurements of the scanning device 110. For example, the user staying at home with reading a book can be differentiated from the user running in the park by merely sensing the amount of motion of the user. For sensing the abstractive visual activities, the scanning device 110 does not necessarily need to perfectly distinguish the visual activities, but to merely recognize signs of changes of the visual activities. In contrast, the concrete visual activities can be measured or derived by the scanning device 110 utilizing the measurements and data stored in a database. Specific procedures for measuring or deriving the concrete visual activities will be described later in this description.

The distance sensing unit 114 may measure one or more distances from the scanning device 110 to one or more objects that exist in the visual activities. When the scanning device 110 is mounted on a head or near the eyes of the user, the distances can be related to viewing distances.

The observation device 130 may acquire the visual activities and the viewing distance profiles of the visual activities from the scanning device 110. The observation device 130 may be implemented to include the scanning device 110. The observation unit 130 may estimate times spent on each of the visual activities.

The input unit 150 may receive or measure personal factors and/or general factors for determining the activity relevance (AR) factor. The AR factor may include at least one of an input of the user, a frequency of spectacle usage and changes, an amount of motion of the user, an illumination in a location of the user and/or general preferences for the spectacle independence. The input unit 150 may be implemented to be included in the observation device 130.

The processor 170 may calculate personal distance profiles based on at least one of the viewing distance profiles for the visual activities (i.e. activity distance profiles), the time spent on the visual activities and/or the activity relevance factor. The personal distance profile may be or include at least one of a statistical distance profile and a preferred distance profile.

The processor 170 may calculate the statistical (time-weighted) distance profile based on the acquired viewing distance profiles for the visual activities. Calculation of the statistical distance profile based on the distance profiles may be performed by simply integrating all the viewing distance profiles of the visual activities. The calculation of the statistical distance profile may further be performed by taking the time spent on the visual activities into account. Specifically, weights that may apply to each of the viewing distance profiles can be defined as the ratios of the estimated time for one of the visual activities to the total time of the visual activities. These weights may be applied (or multiplied) to the viewing distance profiles, respectively, and then the processor 170 may calculate the statistical distance profile.

The statistical distance profile may be defined as $$H_t(P) = \frac{1}{T}\sum_{a \in A} t_a h_a(P),$$

wherein T is the total time of the visual activities, $t_a$ is time spent on a visual activity of the visual activities, P is a viewing distance, an optical power or any distance-related parameter, $h_a(P)$ is a viewing distance profile for the visual activity, a is the visual activity, and A is the visual activities.

The (observed) viewing distance profile may be defined as $h_a(P)$, where P is the viewing distance, optical power/defocus or any distance-related parameter, where h is the frequency of defocus occurrence, and it is assumed that the distance profile is normalised to one as $$\int_{-\infty}^{\infty} h(P)dP = 1.$$

The distance profile for a certain visual activity a may be expressed as $h_a(P)$, wherein a may be the certain visual activity from a set of individual activities A ($a \in A$). The time spent within the certain visual activity a may be expressed as $t_a$ and the total observation time may be T, which may be also defined as $$\sum_{a \in A} t_a = T.$$

The observation unit 130 may acquire activity relevance factors based on parameters including at least one of an input of the user, a frequency of spectacle usage and/or changes, an amount of motion of the user, an illumination in a location of the user and general preferences for the spectacle independence.

The processor 170 may calculate the preferred distance profile based on the activity relevance factors.

The preferred distance profile is defined as $$H_m(P) = \sum_{a \in A} m_a h_a(P),$$

Further, $m_a$ may be an activity relevance factor for a visual activity a, and can be normalised as $$\sum_{a \in A} m_a = 1$$

when a may be the visual activity from a set of individual activities A ($a \in A$).

The implementation unit 190 may customise the optical lens, e.g. the IOL, based on the personal distance profile (including the statistical distance profile and/or the preferred distance profile). The implementation unit 190 may determine the number of focal points needed in at least one of the personal distance profile, determine diopters for the focal points and manufacture the optical lens having the optical power at the focal points. The implementation unit 190 can be equipped separately from the lens customising device 100.

Observation of the visual behaviour can provide the input to a choice of a specific strategy (such as, monofocal, multifocal, monovision or different lenses) for the eyesight correction as well as specific parameters of lenses for the implantation. Such observations can be in the form of direct measurements of the employed distances and/or other vision related parameters, distribution of the time spent for performing various vision related activities or both. Observations are important in terms of identifying vision-related activities, as well as understanding the time spent in those activities (serves as a first indication of importance for the patient), and particular visual requirements during these activities (distance, illumination, head tilt, etc.). For example, working on a computer may demonstrate a significant inter-user variation of employed distances based on the individual preferences and occupation. One patient might prefer to work on a larger screen at correspondingly larger distance, while other patients prefer a laptop screen placed at closer distance.

Figure 2:
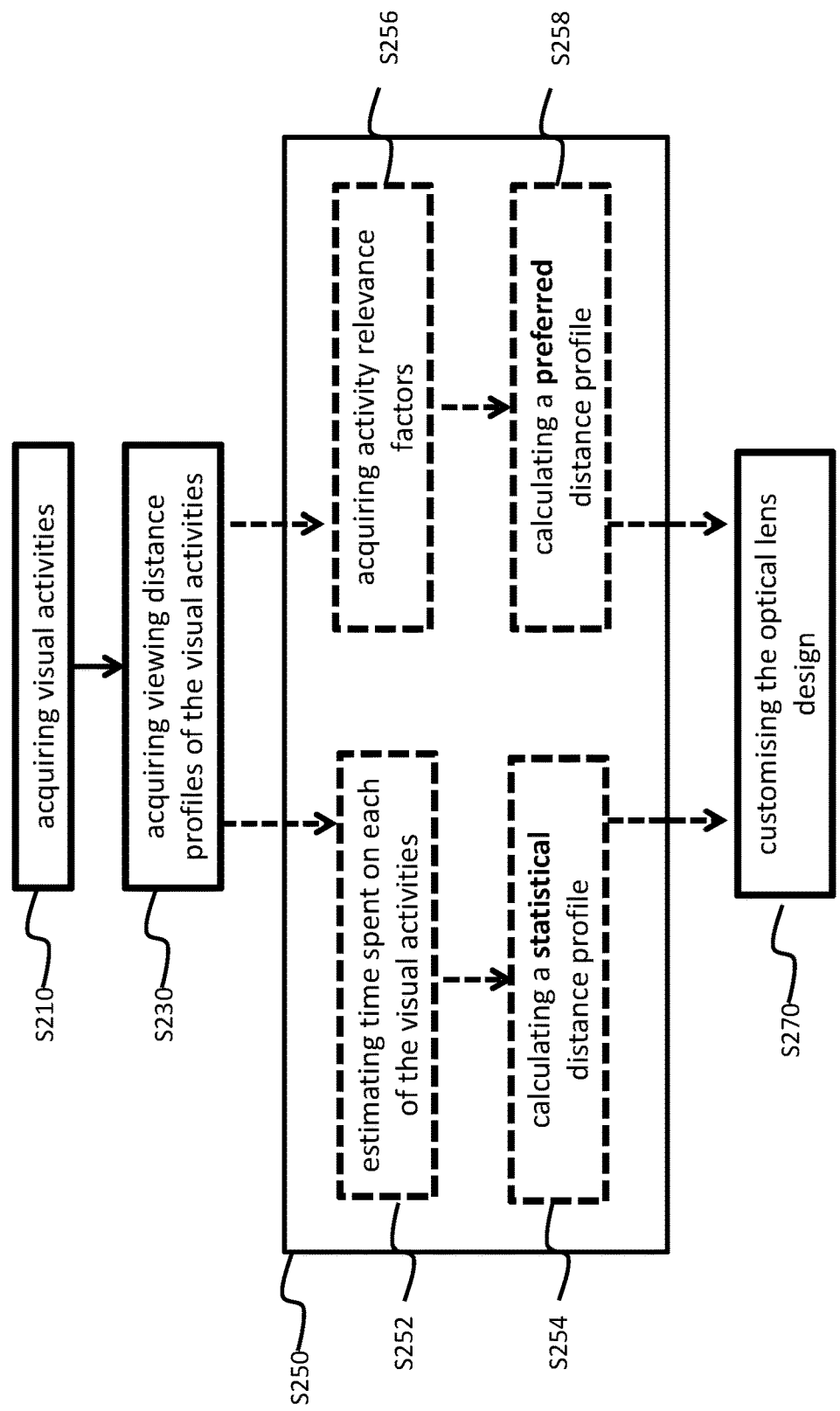
FIG. 2 illustrates a flow diagram corresponding to a method of the present disclosure.

FIG. 2 illustrates a flow diagram corresponding to a method of the present disclosure.

The method may comprise acquiring S210 visual activities of a user, acquiring S230 viewing distance profiles of the visual activities, acquiring S250 a personal distance profile based on the acquired distance profiles, and customising S270 the optical lens based on the personal distance profile. The acquiring S250 the personal distance profile may comprise estimating S252 a time spent on each of the visual activities, and calculating S254 a statistical (time-weighted) distance profile based on the acquired viewing distance profiles and a ratio of the estimated time to total time of the visual activities. A step for calculating the ratio can be included in the method.

The acquiring S250 the personal distance profile may comprise acquiring S256 activity relevance factors based on parameters including at least one of an input of the user, a frequency of spectacle changes, an amount of motion of the user, an illumination in a location of the user and general preferences for the spectacle independence, and calculating S258 a preferred distance profile based on the acquired viewing distance profiles and the activity relevance factors. Details of the method can be supplemented by the description provided above for the lens customising device 100.

Figure 3:
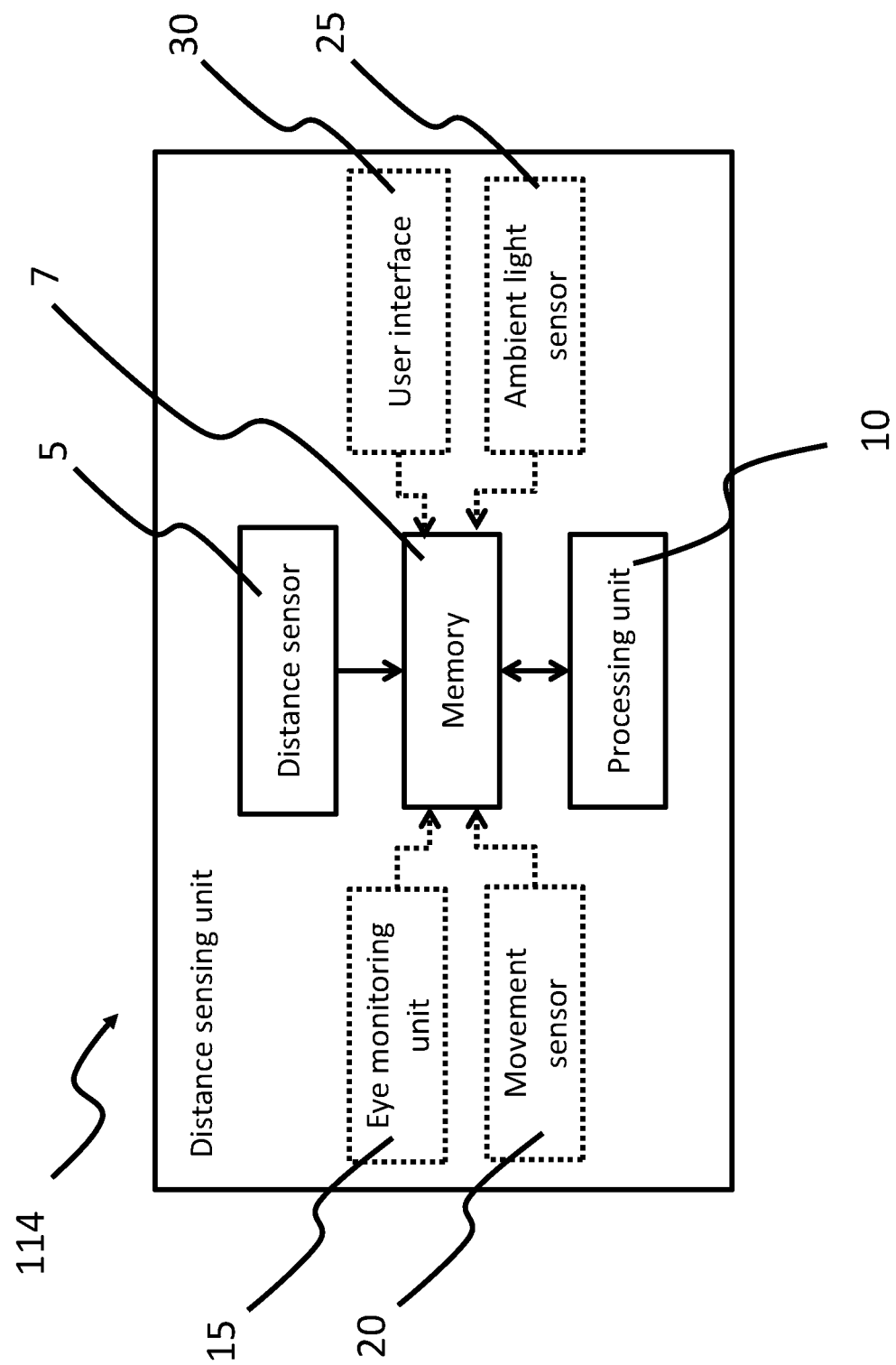
FIG. 3 illustrates an example of a distance sensing unit 114 according to the present disclosure.

FIG. 3 illustrates an example of a distance sensing unit 114 according to the present disclosure.

The distance sensing unit 114 may comprise a distance sensor (or a plurality of distance sensors) 5, a memory unit 7 and/or a processing unit 10. Functions of the memory unit 7 and/or processing unit 10 can be performed by the processor 340 and the memory 330 of the scanning device 110 described above, and the memory unit 7 and/or processing unit 10 may be omitted in the distance sensing unit 114. Optionally, the distance sensing unit 114 may comprise an eye monitor unit 15, a movement sensor 20, an ambient light sensor and/or a user interface 30. The different units 5, 7, 10, 15, 20, 25 of the distance sensing unit 110 can be realised in one and the same device 114 or can be distributed in two or more separate devices to form the distance sensing unit 114.

The distance sensor 5 may measure one or more viewing distances. These distances are distances between a user and one or more objects in the subject's viewing direction. It is possible that the distance sensor 5 may measure the one or more viewing distances actively or passively. Active measurement of the viewing distances may be performed as the distance sensor 5 automatically senses objects in a space where the distance sensing unit 114 is located and measures the viewing distances to the objects. In this case, the viewing distances may be measured without consideration of the user's movements. For passive measurement of the viewing distances, the distance sensor 5 may measure a distance in a certain direction depending on the user's movements. The movements including rotations and/or displacements of the distance sensing unit 114 may be measured by the movement sensor 20. If the distance sensing unit 114 is mounted on a head of a user, the movements may be caused by natural head motions of the user. In case the distance sensor 5 is equipped to sense the viewing distances in the direction of the line of sight of the user for the passive measurement, information for the object which is focused by the user can be acquired. For example, measuring the viewing distance may be performed multiple times to measure distances between the distance sensing unit 114 and multiple points of the object. The viewing distances to the points in addition to directions to the points would result in information on the object's exterior. The information may include a position, a shape, an inclination, a size, a pose and/or a kind of the object. Or the information may include or be topography around or about the object. Deriving the information from the measured viewing distances and directions may be performed by the processing unit 10. It is possible that the visual activity can be derived by the information. For example, the processing unit 10 may classify types of the objects based on the information by comparing the information with reference data stored in the memory 7 regarding possible objects. For example, when the size of the object is similar with typical sizes (reference data) of books and the viewing distances to the object corresponds to typical reading distance (reference data), the processing unit 10 may determine that the visual activity is a reading.

The memory unit 7 may store the measured viewing distances in a set of measured viewing distances. The processing unit 10 determines a statistical distribution of the measured viewing distances from the set of measured viewing distances.

The eye monitoring unit 15 detects, the subject's eye direction relative to the distance measuring sensor's direction, e.g. viewing direction. The eye monitoring unit 15 may sense at least one of coordinated movements of eyes, size of the pupils or change of the lens shape of the user. The eye monitoring unit 15 may determine an accommodation effort using at least one of a vergence derived from the sensed movements of the eyes, the size of the pupils and the change of the lens shape. When human eyes focus on an object, they perform coordinated adjustments in vergence, shape of the lens to change optical power and, correspondingly, focal length and pupil size. For example, monitoring of positions of both eyes can allow detection of the vergence, which is a simultaneous movement of both eyes in the opposite direction. Eyes move towards each other while focusing on near objects and move away of each other while focusing on distant objects. Changes of the shape of the lens can be monitored by tracking the reflections of the probing light from surfaces of the lens (for example, by analysing Purkinje reflections, such as P3 and P4). When focusing on a near object, pupils constrict in order to minimize image blurring. Pupil size can be measured with imaging or any other suitable method. The system can detect the accommodation by detection of pupil size changes. During the detection of the accommodation from pupil size, the system may compensate effects to the size of the pupil due to brightness which may be measured with the context sensors, such as an ambient light sensor. The eye monitoring unit 15 or the processing unit 10 may calculate the viewing distance of the user based on the determined accommodation effort. The viewing distance can be defined as a distance to a point where the user is looking at. By tracking the accommodation effort using any of the mentioned features or a combination of two of more of them: vergence, lens shape change, pupil size, the system can track viewing distances that a user is using.

The processing unit 10 statistically weights, selects or discards the measured viewing distances from the set of measured viewing distances based on the subject's eye direction relative to the distance measuring sensor's direction, e.g. viewing direction. Instead of discarding the measured viewing distances, the processing unit 10 may select specific viewing distances regarded valuable or select a subject's preferred viewing distances or weight the measured viewing distances with a weighting factor smaller or greater than one.

The movement sensor 20 measures movements of the subject's body. In the present example, the movement sensor 20 may or may not comprise an accelerometer and/or a gyroscope, but may or may not further comprise different sensors like a magnetometer, an altimeter, a pedometer or a geopositioning device, for example.

The processing unit 10 statistically weights, selects or discards the measured viewing distances from the set of measured viewing distances based on the measured movements. If a subject's head is at least substantially steadily pointed to a measured object, the distance to the object is measured and weighted by a factor of one or higher than one. If the subject's attention is distracted, e.g. when a subject's head is moving at least substantially constantly around an object, the measured distance is weighted by a factor smaller than 1 or discarded and therefore not considered in the overall statistical distribution.

The ambient light sensor 25, which may be extended by using an additional colour sensor, measures ambient light and/or light intensity and/or spectral content in the subject's viewing direction.

The user interface 30 receives a user input. The subject's input can be tapping on the device, head gestures like nodding or shaking, detected by head motion sensor, subject or eye movement, detected by the eye monitoring device, and the like.

Another example might be a subject putting his or her hands in front of the sensor with a waving hand gesture or keeping his or her hand in front of the distance sensing unit 114 for a few seconds to discard or weight measured viewing distances.

Figure 4:
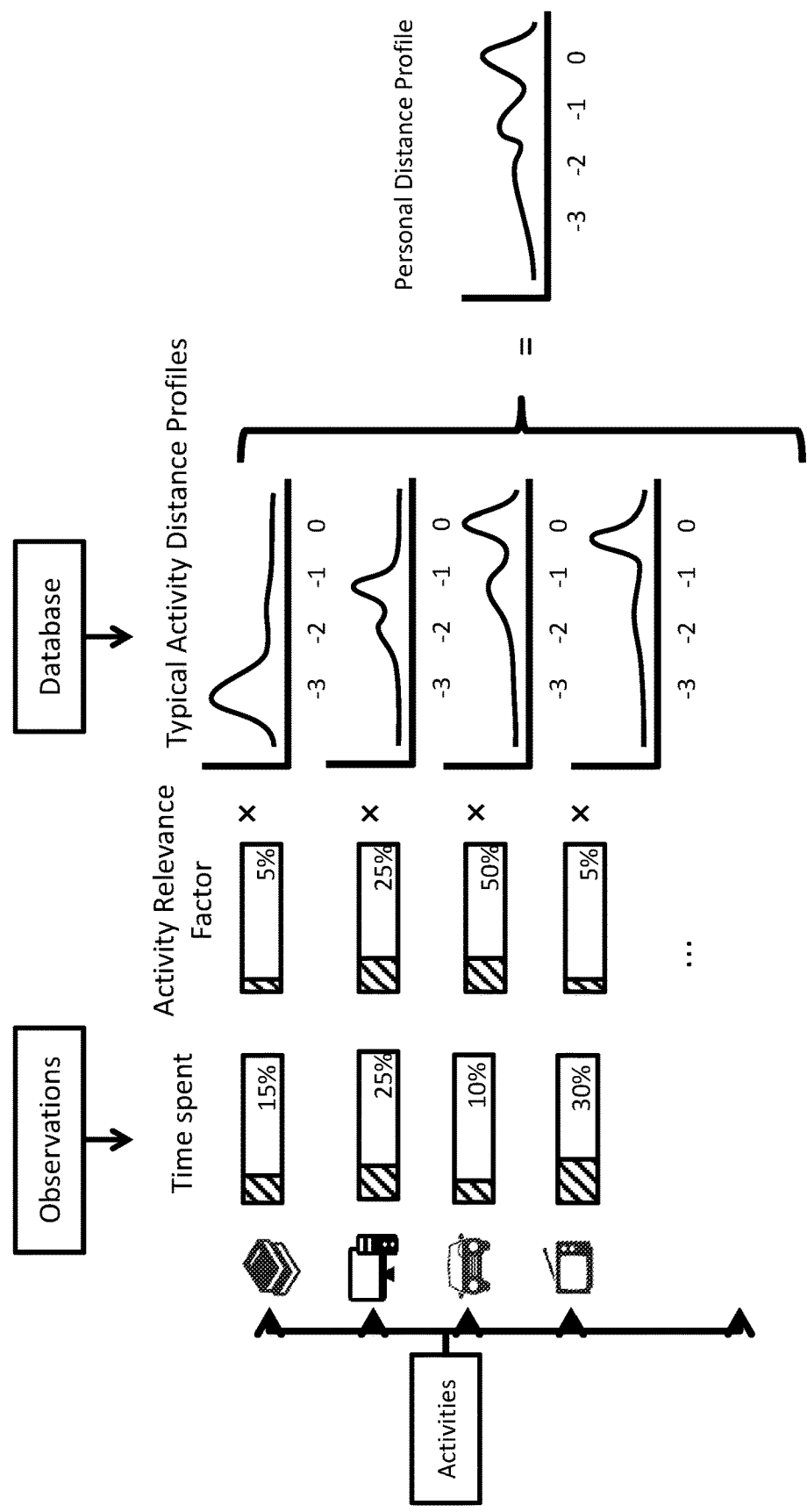
FIG. 4 illustrates a schematic diagram of deriving a personal distance profile regarding visual activities and time spent on the visual activities.

FIG. 4 illustrates a schematic diagram of deriving a personal distance profile regarding viewing distance profiles for visual activities and time spent on the visual activities.

From parameters regarding the visual activities, the most relevant one would be distances to the one or more object shown in the visual activity. Illumination conditions can be also important. Physiological sensors that can be equipped in the lens customising device can measure and provide information about a state of the individual visual system, such as eye tracking, blinking, pupil size, accommodation and/or etc.

According to one example of the present disclosure, an activities-based approach for selecting the optical lens (including IOL) for the patient is provided herein. In this approach, the personal distance profile can be calculated or derived based on typical activity distances profiles employed by users. The typical activity distance profile may be defined as a viewing distance profile typically adopted by the population for a specific visual activity. For example, if the observation identifies that a patient spends significant time reading, an IOL which delivers spectacles independence for near distances may be offered for the patient. In this case, individual reading properties (e.g. preferred reading distance or illumination condition) of the patient may not be reflected to the preferred distance profile.

For this approach, the visual activities can be measured or derived without measuring the viewing distances or producing the viewing distance profile. For instance, the patient may input or select a type of the visual activity when he/she starts to conduct the visual activity. Or the lens customising device may measure viewing distances for a short period, for example just long enough in order to determine the visual activity, but not sufficient for producing the viewing distance profile of the visual activity. A time respectively spent on each of the visual activities can be measured and the ratios of the respective time to the total time may be calculated. The lens customising device may acquire typical activity distance profiles that relate the typical viewing distances for each of the visual activities. Weights derived from the ratios can be applied (or multiplied) to the typical activity distance profiles. The weight applied typical activity distance profiles may be added up to calculated the personal distance profile. The activity relevance factor for each of the visual activities may or may not be considered during the above processes.

Herein, the calculated personal distance profile with the above process can be referred to as a statistical distance profile.

Figure 5:
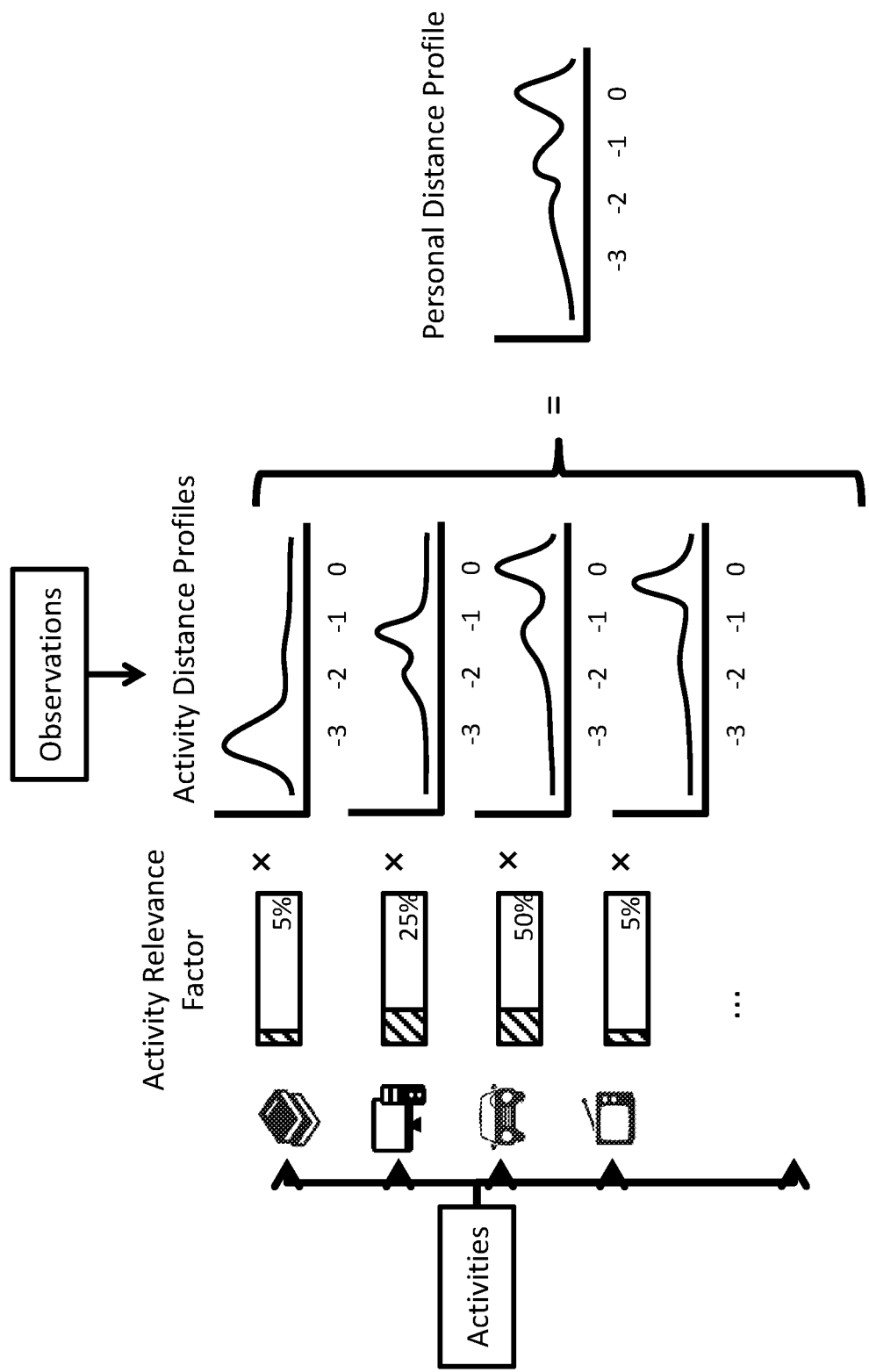
FIG. 5 illustrates a schematic diagram of deriving a personal distance profile regarding activity distance profiles and activity relevance factors.

FIG. 5 illustrates a schematic diagram of deriving a personal distance profile regarding activity distance profiles and activity relevance factors.

A distance statistics approach is capable of understanding distance requirements of the individual user, but would not be capable of taking into account of the activity relevance factors of the individual user. For example, an individual user might be feeling comfortable wearing spectacles during reading and thus the IOL should not necessarily be optimised for a reading-related distance range. A distance statistics approach can be performed by asking the individual user to perform required visual activities while observing the employed viewing distances. This can be done in the clinic or at home.

The lens customising device may recognize the abstractive visual activities. The abstractive visual activities can be measured or derived by merely distinguishing visual activities having significant changes in the measurements of the scanning device. For example, a user staying at home and reading a book can be differentiated from a user running in the park by merely sensing the amount of motion of the user since there would be significant differences in viewing distance profiles. For sensing the abstractive visual activities, the scanning device does not necessarily need to perfectly distinguish the visual activities, but to merely recognize signs of changes of the visual activities. Since the distance statistics approach does not utilize the visual activities, the activity relevance factors significantly related to the characteristics of the visual activities themselves would be inappropriate to be considered during the calculation of the personal distance profile. However, the activity relevance factor that may be derivable or estimated from the environment, such as an illumination, an amount of motion or a spectacle change frequency, can be taken into account for the personal distance profile.

The activity distance profiles gathered during the observation may be added up to calculate the personal distance profile. The activity relevance factors may be considered or not.

Herein, the calculated personal distance profile with the above process can be referred to as a preferred distance profile.

Figure 6:
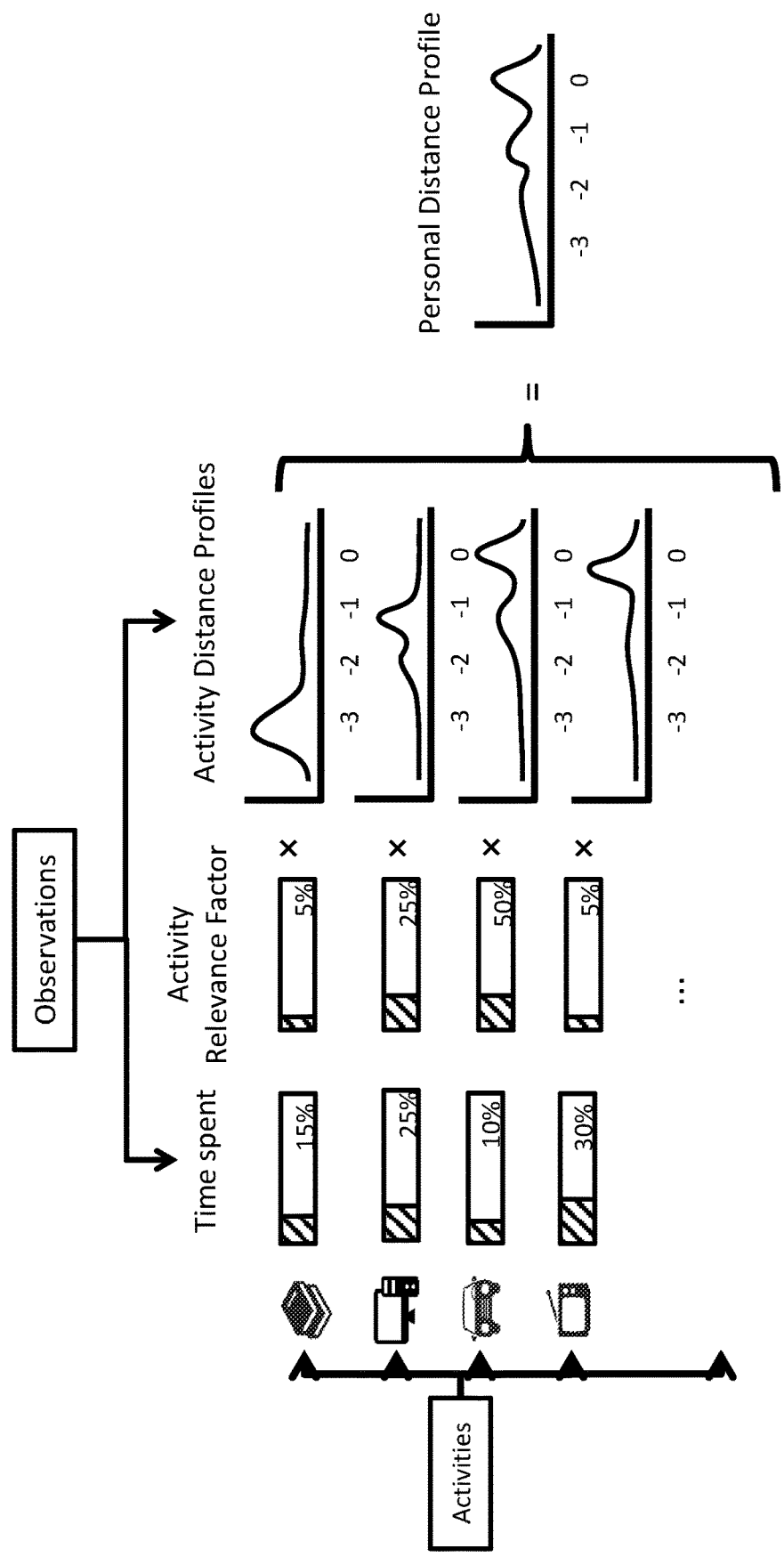
FIG. 6 illustrates a schematic diagram of deriving a personal distance profile regarding activity distance profiles, time spent on visual activities and activity relevance factors.

FIG. 6 illustrates a schematic diagram of deriving a personal distance profile regarding activity distance profiles, time spent on visual activities and activity relevance factors.

The most precise way of identifying the personal distance profile may be to include both the statistical distance profiles and preferred distance profiles. In addition, to improve the preciseness, activity relevance factor derived or estimated for the visual activities may be taken into account.

For this approach, the visual activities can be input by the user or be determined by the lens customising device. Times spent on each of the visual activities and distance profiles for the visual activities may be measured. Weights based on the times spent may be applied to the distance profiles. Weights or AR factors can be additionally applied to the distance profiles. The weighted distance profiles may be added up to produce the preferred distance profile.

Figure 7:
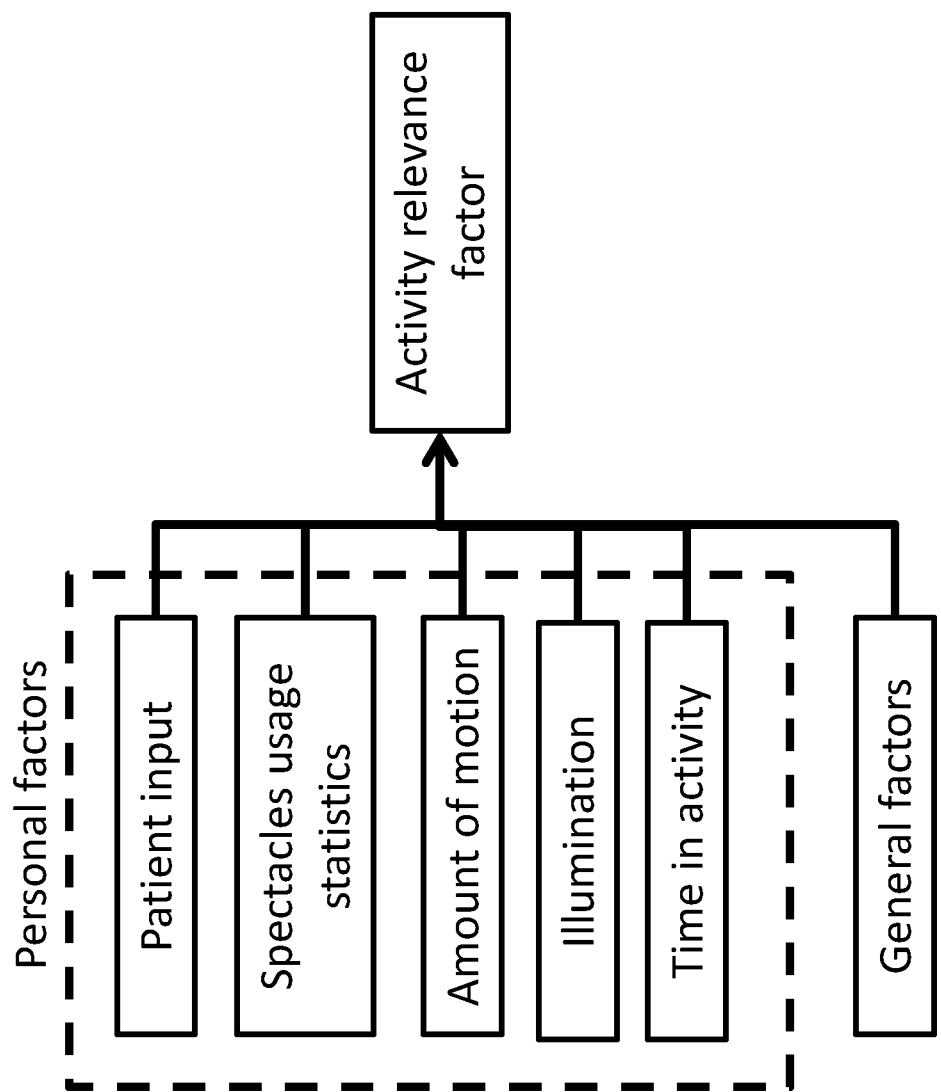
FIG. 7 illustrates a schematic diagram of deriving activity relevance (AR) factors.

FIG. 7 illustrates a schematic diagram of deriving activity relevance factors.

The activity relevance (or the AR factor) may be defined as needs or preferences for use of vision without spectacles. For example, during sport activities, for the reason of comfort, or social activities, for cosmetic reasons, it may be important for the patient or user to be spectacle-free/free of spectacles.

The requirements of the activity relevance may be also referred to as spectacles independence requirement which may be defined as a factor indicating the independence from the spectacles during a specific visual activity. The activity relevance may be required by the patient or user objectively, subjectively or both. The activity relevance can be derived from direct subjective patient input (individual preferences), can be taken as the time spent during observations (direct translation from), can be based on standard generalized distributions and/or can be derived from the observations based on objective spectacles discomfort criteria.

The subjective input by the patient (individual preferences) can be taken before and/or after measurements during the solution planning (as an input thought a GUI of the processing computer program) or in real time during visual activities (through a user interface of the device or accompanying journaling means). Accompanying journaling means can be a mobile application or a traditional notebook. Individual preferences may reflect the requirements from the patient to be spectacles free (spectacles independence). Such requirements can be caused by comfort considerations, like reluctance to wear spectacles during favourite sports activities or during swimming, or by aesthetics considerations, e.g. when the patient would like to appear younger without spectacles.

For example, the discomfort criteria may be inferred by a frequency of changes of the spectacles while performing the visual activities. The change of spectacles can be estimated from the observations (by the observation unit) as the number/frequency of switching between vision zones. For example, driving employs far distance vision for objects outside the car and near/intermediate vision for dashboard as well as dials. Changing spectacles in this situation would be impractical, and a visual correcting solution would be better to target minimisation of the discomfort, hence the AR may be high for such visual activities.

Another example of the objective discomfort criteria can be an amount of vigorous motion during visual activities. The amount of the motion can be estimated from measurements of inertia sensors, such an accelerometer, a gyroscope, a magnetometer, a step counter or etc. or from location tracking sensors which can be equipped in the apparatus. Presence of the vigorous activity would suggest the requirement of the spectacles independence, since it may be difficult for the patient to wear the spectacles in such visual activities. Hence, the AR for this visual activity may be set to a high value.

Yet another example of the discomfort criteria can be the illumination conditions during the visual activities. Illumination conditions during the visual activities are responsible for a change of a patient's pupil size and thus it may be considered when selecting the lens geometry. For example, if a patient is performing visual activities in low light conditions (mesopic or scotopic) and when the pupil is significantly dilated, it is recommendable that the solution for the eyesight correction involves a large optical zone in order to avoid distortions caused by light passing outside of the optical zone of the lens. On contrary, in a well-lighted condition (photopic vision), the pupil would be significantly constricted, which results in extended optical depth of the field and thus allows for higher tolerance to visual defocus. Thus, the vision correcting strategy might be (fine) tuned to benefit activities/distances for the low-light conditions, while compromising on the activities/distances performed in bright-light.

Visual activities performed in low-light are likely more vision demanding and would require better vision optics to provide a sharp vision, while visual activities in bright-light are more defocus-tolerant. The colour content of image-forming light may also influence the contrast sensitivity of an eye. Thus, discomfort criteria would be higher for the low-light visual activities and lower for the bright-light visual activities. Hence, the AR for the low-light visual activities may be set to a higher value, and the AR for the bright-light visual activities may be set to a relatively lower value.

Extended periods of a vision activity with limited motion would result in low objective discomfort with spectacles, and thus lead to a low AR factor. Such visual activity can be reading, working on the desktop PC, watching TV, or etc.

One can also use general (population-derived) preferences (i.e. general factors) for the spectacle independence in the visual activities as the AR. For example, if a majority of the population chooses spectacle independence during tennis (sport activity), a high AR value can be assigned to this visual activity. General preferences can be stored in a predefined (statistics) database, where data is updated from external sources (like a manual input or automatically updated from external databases). Alternatively, general preferences can be stored in a dynamic database updated by the system (e.g. the lens customising device) itself based on other inputs to the AR, like other patients' inputs or discomfort criteria. In a more general manner, observations of a patient behaviour can be collected as a set of sensor measurements, which further serve as inputs to the algorithm which automatically assigns an individual to one of the typical groups and thus derives a solution/strategy optimal for such a group.

Figure 8:
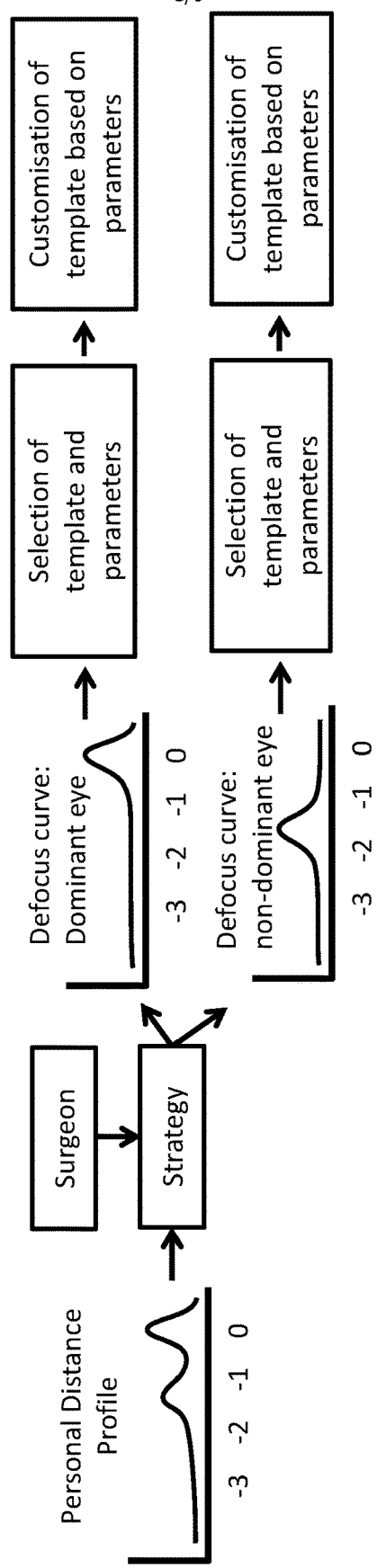
FIG. 8 illustrates procedures for selecting suitable optical lenses.

FIG. 8 illustrates procedures for selecting suitable optical lenses.

Based on the personal distance profiles, the implementation strategy for the IOL may be decided. The goal is to fit the available solutions (e.g. IOL, spectacles, contact lens) with the personal distance profile which may be defined as $H_m(P)$, $H_t(P)$ or both of them. Additional parameters, such as illumination and restrictions of the solutions, can be taken into account in accordance with personal preferences/restrictions to fit the available solutions with the personal distance profile. For example, a surgeon might exclude a strategy based on diffractive optics if a patient has the need for driving at night.

The strategy may imply selection of the type of lens, for example, monofocal, multifocal, extended depth of focus, toric, or etc. and/or the parameters. Based on the selected strategy, the templates may be chosen and the specific parameters, like e.g. add power of second focus are defined and entered into the lens customising device. The selection of the template for the desired strategy and profile can be done automatically. Traditional factors (i.e. individual eye parameters) for correcting the vision of the patient may be taken into account for the selection.

Multifocal lenses allows to focus light on the retina from more than a single distance and thus enable a patient to have objects from multiple distances in focus. An IOL is characterised by a so-called defocus curve, which indicates an optical performance of the vision (visual acuity) as a function of defocus in Diopters [D]-difference in optical power from focus on infinity. For a monofocal lens a single focus exists in the predetermined distance, for example in infinity, which corresponds to defocus of 0. The personal distance profile described above may be utilized to characterize a monofocal or multifocal IOL. That is, based on the defocus curve obtained from the personal distance profile, a lens with specific defocus characteristics may be manufactured.

Such lens customisation (production/manufacturing/machining) can be performed by modifying the geometry of the lens and/or optical properties, like locally modifying an refractive index. Geometry/morphology manufacturing/adjustment can be achieved with additive manufacturing process, like 3D printing, or with traditional subtractive manufacturing, when material is removed from the template in order to reach a required geometry. A modification of the geometry can be done by a local adjustment of mechanical properties, like adding or releasing tension to affect the overall lens geometry. In another implementation of a subtractive process laser-based ablation can be performed in order to achieve the required geometry. In yet another scenario, ultraviolet radiation (photo) can be applied to induce cross-linking of a polymer matrix.

Design/customisation of the lens may imply an adjustment of a lens or at least one of components of a multi-component lens, as well as a selection of a composition of the multi-component lens. A modification of geometry of the IOL, by modification of optical properties (photopolymerisation or liquid crystal approach), or magnetic adjustment can be included in the customisation.

The optical lens may be any of the natural optical elements of an eye, e.g. cornea or lens. In this case adjustment can performed with a laser, for example by ablating the corneal surface or making corneal incisions for refractive correction or by modifying mechanical properties of the natural lens for presbyopia treatment. Customisation of corresponding ablation and treatment settings such as geometry and parameters of applied laser pulses can be performed based on viewing distance profiles.

The above described processes for customising the optical lens may be utilized before and/or after an implantation of the optical implants such as IOLs. Technologies for manufacturing before implantation may be 3D printing (adding lens material), ablation of the template matrix (removal of the lens material), chemical and photochemical cross-linking/photopolymerisation (modification of lens material, which also induces a change in geometry), a modification of the refractive index (e.g. with femto-second laser light) or any combination of those. Technologies for adjusting the existing lenses based on the personal distance profile may be a multicomponent IOL, a mechanically adjustable IOL or a repeatedly adjustable IOL in case of invasive adjustment, and light adjustable lenses, magnetic adjustment, liquid crystal with wireless control, femtosecond laser adjustment or 2-photon chemistry in case of non-invasive adjustment.

Statistics of personal distance profiles from a group of users can be used as an input to development of lenses or templates for the large-scale production. For example, by analysing distance profiles it is possible to optimise offering of pre-shaped lens templates in order to minimise tuning or make tuning unnecessary, if the pre-shaped template is capable of fitting patient requirements. By collecting statistics of the distance profiles from multiple users it is possible to determine visual needs which are not adequately addressed by the existing selection of pre-shaped lenses and with this information add or modify designs of produced pre-shaped lenses to address those needs.

This is especially useful when lens tuning equipment is not available and user has to be fitted with the existing pre-shaped lenses.

Figure 9:
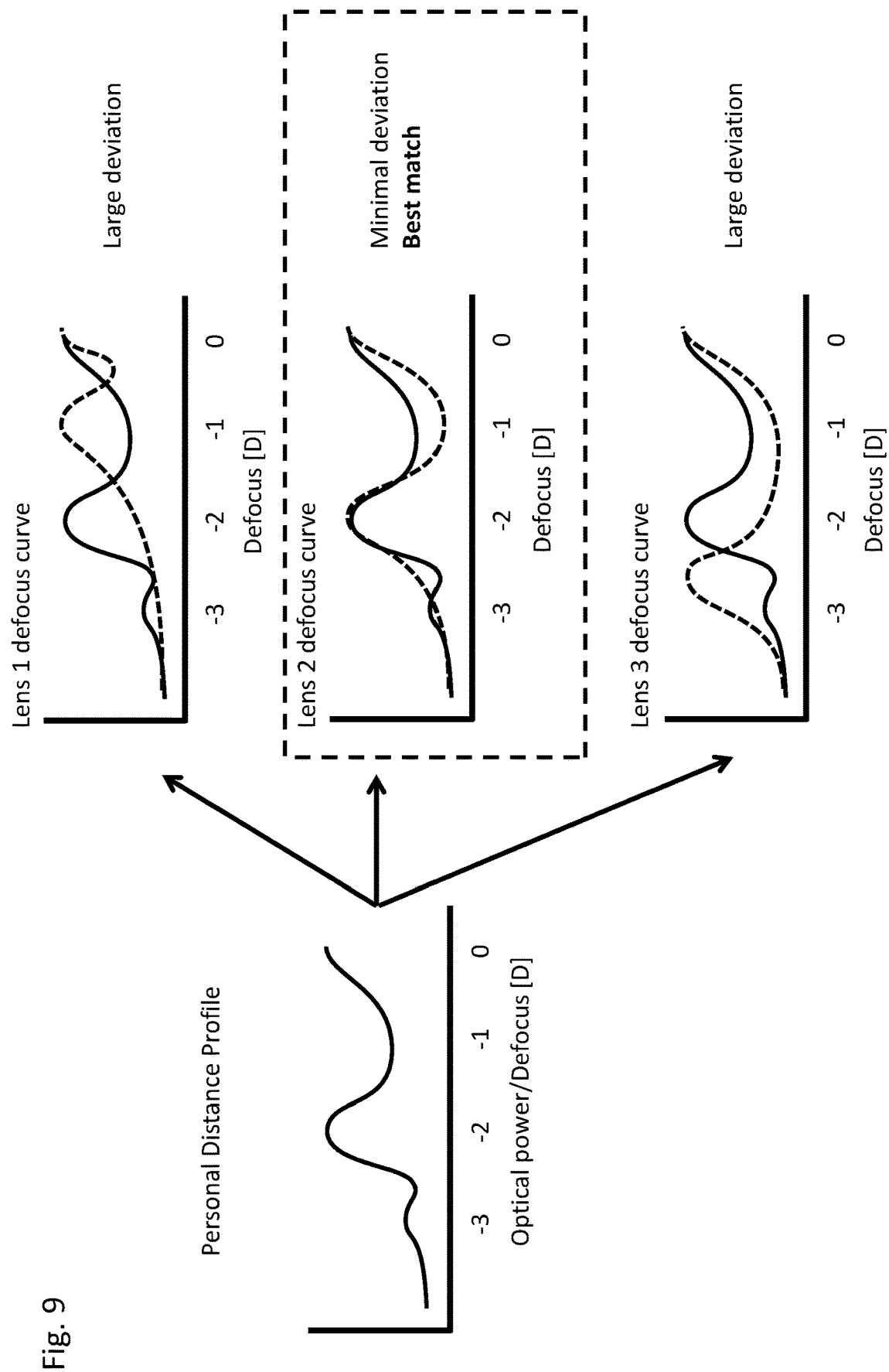
FIG. 9 illustrates a selection of IOL by matching the personal distance profile with characteristics of optical lenses.

FIG. 9 illustrates a selection of IOL by matching the personal distance profile with characteristics of optical lenses.

The personal distance profile is obtained statistically by time-weighting of visual activities and/or based on the activity relevance-preferred. In the presented example, a personal distance profile has 2 peaks in the positions of 0 defocus (first peak), corresponding to infinite distance and on −2D (second peak), corresponding to 0.5 m viewing distance. For implementation of the required profile multiple options may exist, characterised by the optical quality/vision acuity as a function of optical power (defocus curve). The presented examples of defocus curves are different in the optical power (or position) of the second peak, but all have a peak at the infinite distance (0 defocus). In the presented example, broken lines show the characteristics of the lenses, such that lens 1 has a peak at −1D defocus (also called add-power), lens 2 has add-power of −2D and lens 3 has add-power of −3D. The matching can be performed by fitting the defocus curves to the personal distance profile with the proper vertical scaling. As shown in the example, the fitting of lenses 1 and 3 results in large deviation, measured for example by mean square error, root mean square error or any other statistical metric. The lens 2 has the minimal deviation from the evaluated options and thus represents the best match. The selection of the best match can be done automatically, by fitting plurality of defocus curves from the available database to the personal distance profiles. As an output it can provide surgeon with the best options for the IOL for a particular patient. It can also include additional parameters for the selection of the best lens, such as preferences of the surgeon for the IOLs, previous history of the selected IOLs, patients feedback on the implanted IOLs, availability, costs and/or lens qualities, etc.

By way of the technique described herein, it is possible to efficiently and precisely customise/design/adjust/manufacture an optical lens in compliance with the needs of the patient or user or a group of patients/users.

It will be understood that the embodiments described above are merely exemplary and that the principles of the present disclosure may be practiced in other implementations.

It is believed that the advantages of the technique presented herein will be fully understood from the foregoing description, and it will be apparent that various changes may be made in the form, constructions and arrangement of the exemplary aspects thereof without departing from the scope of the disclosure or without sacrificing all of its advantageous effects. Because the technique presented herein can be varied in many ways, it will be recognized that the disclosure should be limited only by the scope of the claims that follow.

The invention claimed is:

1. An apparatus for customising an optical lens, the apparatus comprising:
   an observation unit adapted to acquire occurrence distributions of visual activities of a user;
   a processor adapted to acquire a personal distance profile based on the acquired occurrence distributions; and
   an implementation unit adapted to customise the optical lens based on the acquired personal distance profile,
   wherein each of the occurrence distributions relates to a specific visual activity of the visual activities,
   wherein the personal distance profile includes or is at least one of a statistical distance profile and a preferred distance profile, and
   wherein the statistical distance profile is defined as:

$$H_t(P) = \frac{1}{T}\sum_{a \in A} t_a h_a(P),$$

wherein T is the total time of the visual activities, $t_a$ is a time spent on a visual activity a of the visual activities A, P is a viewing distance, an optical power or any distance-related parameter, $h_a(P)$ is an occurrence distribution for the visual activity, a is the visual activity, and A is the visual activities.

2. The apparatus of claim 1,
   wherein the observation unit is further adapted to estimate a time spent on each of the visual activities, and
   wherein the processor is further adapted to calculate the statistical distance profile based on the acquired occurrence distributions and a ratio of the estimated time to total time of the visual activities.

3. The apparatus of claim 1,
   wherein the observation unit is further adapted to acquire activity relevance factors based on parameters including at least one of an input of the user, statistics of spectacles usage, an amount of motion of the user, an illumination in a location of the user and general preferences for spectacle independence, wherein the processor is further adapted to calculate the preferred distance profile based on the acquired occurrence distributions and the acquired activity relevance factors.

4. The apparatus of claim 1, wherein the preferred distance profile is defined as:

$$H_m(P) = \sum_{a \in A} m_a h_a(P),$$

wherein $m_a$ is an activity relevance factor and is normalised as $$\sum_{a \in A} m_a = 1$$

when a is the visual activity and A is the visual activities, wherein P is a viewing distance, an optical power or any distance-related parameter, and $h_a$ (P) is an occurrence distribution for the visual activity.

5. The apparatus of claim 1, wherein the acquired occurrence distributions are of actual activity distance profiles, and wherein the actual activity distance profiles are measured while the user performs the visual activities.

6. The apparatus of claim 1, further comprising:
an activity sensing unit adapted to:
measure distances to a plurality of points of at least one object;
determine orientations and/or positions of the activity sensing unit;
derive information about the at least one object based on the measured distances and the determined orientations and/or positions; and
classify the visual activities of the user based on the derived information, and
wherein the information about the at least one object comprises or is at least one of a position, a shape, an inclination and a size of the object.

7. The apparatus of claim 1, wherein the implementation unit is adapted to:
determine the number of focal points needed in at least one of the statistical distance profile and the preferred distance profile;
determine optical power for the focal points; and
manufacture the optical lens having the determined optical power at the focal points.

8. The apparatus of claim 1,
wherein the optical lens is any of an ophthalmic implant and an ophthalmic lens,
wherein the ophthalmic lens is one of an intraocular lens, a contact lens and a spectacles lens.

9. A method for customising an optical lens, the method comprising:
acquiring occurrence distributions of viewing distances of visual activities;
acquiring a personal distance profile based on the occurrence distributions; and
customising the optical lens based on the acquired personal distance profile,
wherein each of the occurrence distributions relates to a specific visual activity of the visual activities,
wherein the personal distance profile includes or is at least one of a statistical distance profile and a preferred distance profile, and wherein the method further comprises:
estimating a time spent on each of the visual activities; and
calculating the statistical distance profile based on the acquired viewing distance profiles and a ratio of the estimated time to total time of the visual activities; and/or
the method further comprising:
acquiring activity relevance factors based on parameters including at least one of an input of the user, a statistics of spectacles usage, an amount of motion of the user, an illumination in a location of the user and general preferences for spectacle independence;
calculating the preferred distance profile based on the acquired viewing distance profiles and the acquired activity relevance factors; and/or
wherein the statistical distance profile is defined as:

$$H_t(P) = \frac{1}{T} \sum_{a \in A} t_a h_a(P),$$

wherein T is the total time of the visual activities, $t_a$ is a time spent on a visual activity a of the visual activities A, P is a viewing distance, an optical power or any distance-related parameter, $h_a$ (P) is an occurrence distribution for the visual activity, a is the visual activity, and A is the visual activities; and/or
wherein the preferred distance profile is defined as:

$$H_m(P) = \sum_{a \in A} m_a h_a(P),$$

wherein $m_a$ is an activity relevance factor and is normalised as $$\sum_{a \in A} m_a = 1$$

when a is the visual activity and A is the visual activities,
wherein P is a viewing distance, an optical power or any distance-related parameter, and $h_a$ (P) is an occurrence distribution for the visual activity.

10. The method of claim 9, wherein customising the optical lens comprises:
determining the number of focal points needed in at least one of the statistical distance profile and the preferred distance profile;
determining optical power for the focal points; and
manufacturing the optical lens having the optical power at the focal points.

11. The method of claim 9, wherein the method is performed for a group of users and comprises:
acquiring personal distance profiles for the group of users; and
customising the optical lens based on statistical processing of the acquired personal distance profiles for the group of users.

12. An apparatus for customising an optical lens, the apparatus comprising:
- an observation unit adapted to acquire occurrence distributions of visual activities of a user;
- a processor adapted to acquire a personal distance profile based on the acquired occurrence distributions; and
- an implementation unit adapted to customise the optical lens based on the acquired personal distance profile,
- wherein each of the occurrence distributions relates to a specific visual activity of the visual activities,
- wherein the personal distance profile includes or is at least one of a statistical distance profile and a preferred distance profile, and
- wherein the preferred distance profile is defined as:

$$H_m(P) = \sum_{a \in A} m_a h_a(P),$$

wherein $m_a$ is an activity relevance factor and is normalised as $$\sum_{a \in A} m_a = 1$$

when a is the visual activity and A is the visual activities,
wherein P is a viewing distance, an optical power or any distance-related parameter, and $h_a(P)$ is an occurrence distribution for the visual activity.

* * * * *